United States Patent
Sequeira et al.

(10) Patent No.: US 6,204,668 B1
(45) Date of Patent: Mar. 20, 2001

(54) DC/RF BLOOD CELL DETECTOR USING ISOLATED BRIDGE CIRCUIT HAVING AUTOMATIC AMPLITUDE AND PHASE BALANCE COMPONENTS

(75) Inventors: Melwyn F. Sequeira, Plantation; Mirjana Milosevic-Kvajic, Miami Beach; Isay Goltman, Fort Lauderdale, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/255,246

(22) Filed: Feb. 22, 1999

(51) Int. Cl.[7] .................. G01N 27/60; G01N 27/00; G01N 27/06
(52) U.S. Cl. .............. 324/453; 324/71.1; 422/82.02
(58) Field of Search .................... 324/453, 71.4, 324/71.1, 601, 725, 663, 673, 680, 692, 693, 706, 717; 422/82.02; 377/12

(56) References Cited
U.S. PATENT DOCUMENTS

| 2,349,992 | * | 5/1944 | Schrader | 324/698 |
|---|---|---|---|---|
| 3,502,974 | | 3/1970 | Coulter et al. | 324/71 |
| 3,921,066 | * | 11/1975 | Angel et al. | 377/12 |
| 4,298,836 | | 11/1981 | Groves et al. | 324/71 |
| 4,525,666 | | 6/1985 | Groves | 324/71.1 |
| 4,791,355 | | 12/1988 | Coulter et al. | 324/71.1 |
| 5,087,574 | * | 2/1992 | Bell et al. | 436/120 |

* cited by examiner

Primary Examiner—Safet Metjahic
Assistant Examiner—Anjan K Deb
(74) Attorney, Agent, or Firm—Charles E. Wands; Mitchell E. Alter

(57) ABSTRACT

A differential DC/RF bridge-configured flowcell particle detector includes a flowcell and an adjustable circuit model of the flowcell, which are differentially coupled through output amplifier circuits and galvanically isolated from sources of signal degradation. The output of the difference amplifier is coupled to a DC/RF discriminator and associated downstream processing circuitry. Respective amplitude and phase outputs of the DC/RF discriminator are used to control amplitude and phase adjustment circuits of the adjustable circuit model, so as to automatically track amplitude and phase variations in the non-linear behavior of the flowcell, to mirror the characteristic impedance of the flowcell, thereby making the bridge insensitive to variations in the flowcell.

16 Claims, 5 Drawing Sheets

DC/RF BLOOD CELL DETECTOR USING ISOLATED BRIDGE CIRCUIT HAVING AUTOMATIC AMPLITUDE AND PHASE BALANCE COMPONENTS

FIELD OF THE INVENTION

The present invention relates in general to detectors of the type used for conducting electrical measurements of parameters of objects, such as but not limited to the detection of particles (e.g., blood cells) contained in a carrier fluid supplied to a hematology analyzer. The invention is particularly directed to a new and improved DC/RF bridge-configured object parameter detector having an automatic amplitude and phase balance circuit that models the behavior of the object, particularly an object having non-linear characteristics, and compensates for (non-linear) variations in conditions other than the parameter being measured.

BACKGROUND OF THE INVENTION

As an adjunct to the diagnosis and treatment of disease, the medical industry commonly employs various types of particle flow systems, such as that diagrammatically illustrated in FIG. 1, to analyze particles or cells in a patient's body fluid (e.g., blood cells). To this end, a carrier fluid (e.g., saline) stream 1, containing particles/cells 2 of a centrifuged blood sample stored in a blood sample holding chamber 3, is directed along a flow channel 4 through a restricted flowcell 'measurement' aperture 5 of a flowcell 6 into a receiving chamber 7. The flowcell measurement aperture 5 is sized and configured to allow the particles to be counted one at the time as they pass through the flowcell, and includes a pair of electrodes 8 and 9, to which a DC electrical field for measuring the size or volume of each particle and an RF field for measuring the density of each particle passing through the flowcell aperture 5 are applied.

In particular, the dimensions of the flowcell measurement aperture 5 define a "steady state" flowcell characteristic impedance $R_a$, which may be represented by a single capacitance and resistance value at the frequency of interest. As particles pass through the flowcell measurement aperture 5, they introduce changes in the resistance of the flowcell in proportion to their size or volume. These changes in aperture resistance are reflected as DC voltage pulses at the electrodes 8 and 9, and can be measured directly.

In addition, the density or opacity of a blood cell or particle is reflected as a change in the reactance of the flowcell aperture, and has been conventionally measured by coupling the electrodes 8 and 9 in parallel with the resonance (LC tank) circuit of an associated RF oscillator-detector circuit 10. This change in reactance of the flowcell causes a corresponding change in the operation of the RF oscillator, which can be measured by means of an RF pulse detector/demodulator. For an illustration of non-limiting examples of U.S. patent literature detailing such conventional oscillator-based flowcell RF detector circuits attention may be directed to the U.S. patents to Coulter et al, U.S. Pat. No. 3,502,974; Groves et al, U.S. Pat. No. 4,298,836; Groves et al, U.S. Pat. No. 4,525,666; and Coulter et al, U.S. Pat. No. 4,791,355.

Now although an RF oscillator-based flowcell measurement circuit of the type generally shown in FIG. 1 is effective to provide an indication of both size and density of each blood cell, it suffers from a number of problems which are both costly and time-consuming to remedy. One fundamental shortcoming is the fact that the particle detection mechanism was originally designed as and continues to be configured as a tube-based RF Hartley oscillator circuit. This potentially impacts circuit availability, as the number of manufacturers of vacuum (as well as gas filled) electronic tubes continues to decline.

In addition, the effective lifetime of a newly purchased and installed tube in the Hartley oscillator is not only unpredictable, but experience has shown that the effective functionality of most tubes within the Hartley oscillator—detector circuit is very limited, (even though a tube tester measurement shows a tube to be good). At best a tube can expect to last somewhere in a range of three to nine months—and typically involves on the order of two repair/maintenance service calls per year per flowcell.

SUMMARY OF THE INVENTION

In accordance with the present invention, rather than use a change-in-reactance based, RF Hartley oscillator-configured detector to measure particle/cell density, both cell volume and internal cellular conductivity are measured by a DC/RF-stimulated bridge detector. The bridge detector of the invention has a circuit configuration generally of the type employed in a Wheatstone bridge, and uses opto-isolator components for galvanic isolation from sources of signal degradation that might otherwise substantially impair the ability of the bridge to conduct accurate particle detection measurements.

Like a conventional Wheatstone bridge, the DC/RF-driven bridge of the invention includes a first voltage divider branch, in which the object being monitored (e.g., a flowcell) is installed. The first branch of the bridge also includes a linear impedance element connected in a series circuit path between bridge stimulation terminals, across which a high frequency voltage (on the order of several tens of MHz), and a DC excitation voltage are applied. Also coupled in circuit with the flowcell and one of the stimulation terminals is an automatic amplitude and phase balancing, non-linear network (such as a resistor-capacitor network).

The DC/RF stimulated bridge detector of the invention also has a second voltage divider branch containing a flowcell circuit model, which mirrors the impedance of the actual flowcell, and another linear impedance element connected in a series circuit path between the bridge stimulation terminals. The flowcell circuit model functions as an automatic amplitude and phase balance circuit, and comprises an adjustable non-linear network, such as, but not limited to a variable capacitor and a linear resistor coupled in circuit between the high frequency voltage terminal and a bridge output node. The linear resistance elements of the DC/RF bridge of the invention virtually eliminate second order Laplacian effects associated with coupling amplifier circuits. The input capacitance of each coupling amplifier circuit—together with the linear resistor—forms a first order filter having a cut-off frequency defined by the values of the resistor and the input capacitance of an associated coupling amplifier.

A first bridge output node is coupled to a first current gain amplifier, whose output is coupled to a difference amplifier. The difference amplifier is also coupled to the output of a second current gain amplifier, the input of which is coupled to a second bridge output node. This differential amplifier connection effectively cancels inherent common-mode noise, as well as residual noise caused by the imbalance in the two branches of the bridge. The output of the difference amplifier is coupled to a DC/RF discriminator and associated downstream processing circuitry.

By virtue of opto-isolator coupling and its isolated self-powered architecture, the modified Wheatstone bridge detector of the invention is effectively a "floating" bridge, that galvanically isolates the front-end signal detection circuits from very high frequency noise components sourced from the RF oscillator. As a result, filter bandwidths in the downstream signal processing circuits can be made much wider to accommodate all of the signal energy density, with virtually no interference from RF noise in the detected signal path.

A fundamental drawback of a standard Wheatstone bridge network is the degradation of signal quality, and a complete loss of signal in cases involving very high frequency detection schemes, such as RF pulse detection in a flowcell. This signal degradation is mainly due to resistances and reactances parasitic in the interconnect components. For a properly functioning RF pre-amplifier, the parasitics inherent in the bridge must be virtually eliminated. This is effectively accomplished in the invention by using commercially available high noise rejection components, that allow parasitic-minimizing, flip-chip technology using a bare IC die that virtually eliminates capacitive reactance with bridge components, thereby making the bridge virtually immune to signal loading by parasitic capacitance of the coupling circuits.

In addition to 'floating' the network and using flip-chip mounting, the bridge's automatic amplitude and phase balancing circuits serve to track variations in the behavior of the flowcell, which has non-linear (both resistive and capacitive) characteristics, and is susceptible to continuous impedance changes due to temperature, and conductivity of a fluid through its measurement aperture. These amplitude and phase balancing circuits automatically 'tune' their resistive and capacitive elements to mirror the behavior of the flowcell in response to environmental conditions, so as to minimize common mode noise generated by the network, and optimize the signal-to-noise ratio. This automatic phase and amplitude adjustment thus makes the bridge virtually immune to flowcell load tolerances and varying impedances due to the environment.

DETAILED DESCRIPTION

As described briefly above, in accordance with the present invention, both cell volume and internal cellular conductivity are readily measurable by means of a galvanically isolated, Wheatstone bridge-configured DC/RF detector. In order to fully appreciate the manner in which the bridge-based particle detector of the invention is able to perform very sensitive cell measurements in the presence of substantial noise inputs from both the environment and the components of the circuit itself, it is initially useful to review the fundamental circuit configuration and operation of a conventional Wheatstone bridge.

Figure 2:
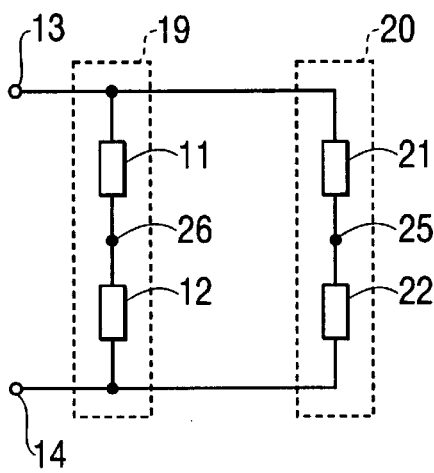
FIG. 2 diagrammatically illustrates the circuit configuration of a Wheatstone bridge.

The basic circuit configuration of a Wheatstone bridge is diagrammatically shown in FIG. 2 as comprising a first voltage divider branch 19 containing a pair of circuit (impedance) elements 11 and 12, that are connected in series between bridge stimulation terminals 13 and 14, and a second voltage divider branch 20 containing a pair of impedance elements 21 and 22 connected between terminals 13 and 14. For stimulating the bridge a current or voltage source, either AC or DC, is applied to terminals 13 and 14.

The two voltage divider branches 19 and 20 form a dual voltage divider network, in which three of the elements, such as impedance elements 11, 12 and 21, are typically implemented as linear circuit components such as resistors, having fixed characteristic values (resistance). The remaining (fourth) element 22, which may also be a linear element, has a parameter that varies as a function of the environment being measured by the network.

In a static condition, the Wheatstone bridge operates so as maintain electrical equilibrium of its two branches; i.e. with all four impedance elements being equal, the differential between network output terminals 25 and 26 will be zero. However, a change in either voltage or current proportional to the change in the value of the variable impedance element 22 will cause the bridge to fall out of its electrical equilibrium, which is detected as a non-zero voltage level at the outputs 25 and 26 of the bridge. The magnitude of this change may then be calculated and processed using conventional downstream-coupled amplification circuitry.

Figure 1:
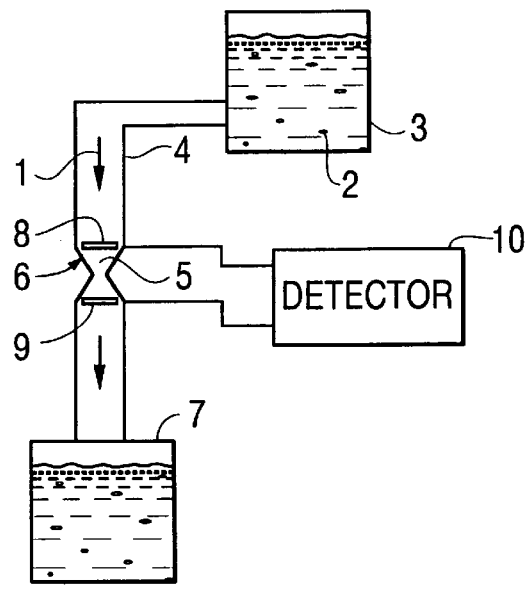
FIG. 1 diagrammatically illustrates a particle (blood cell) flow analyzer.
Figure 3:
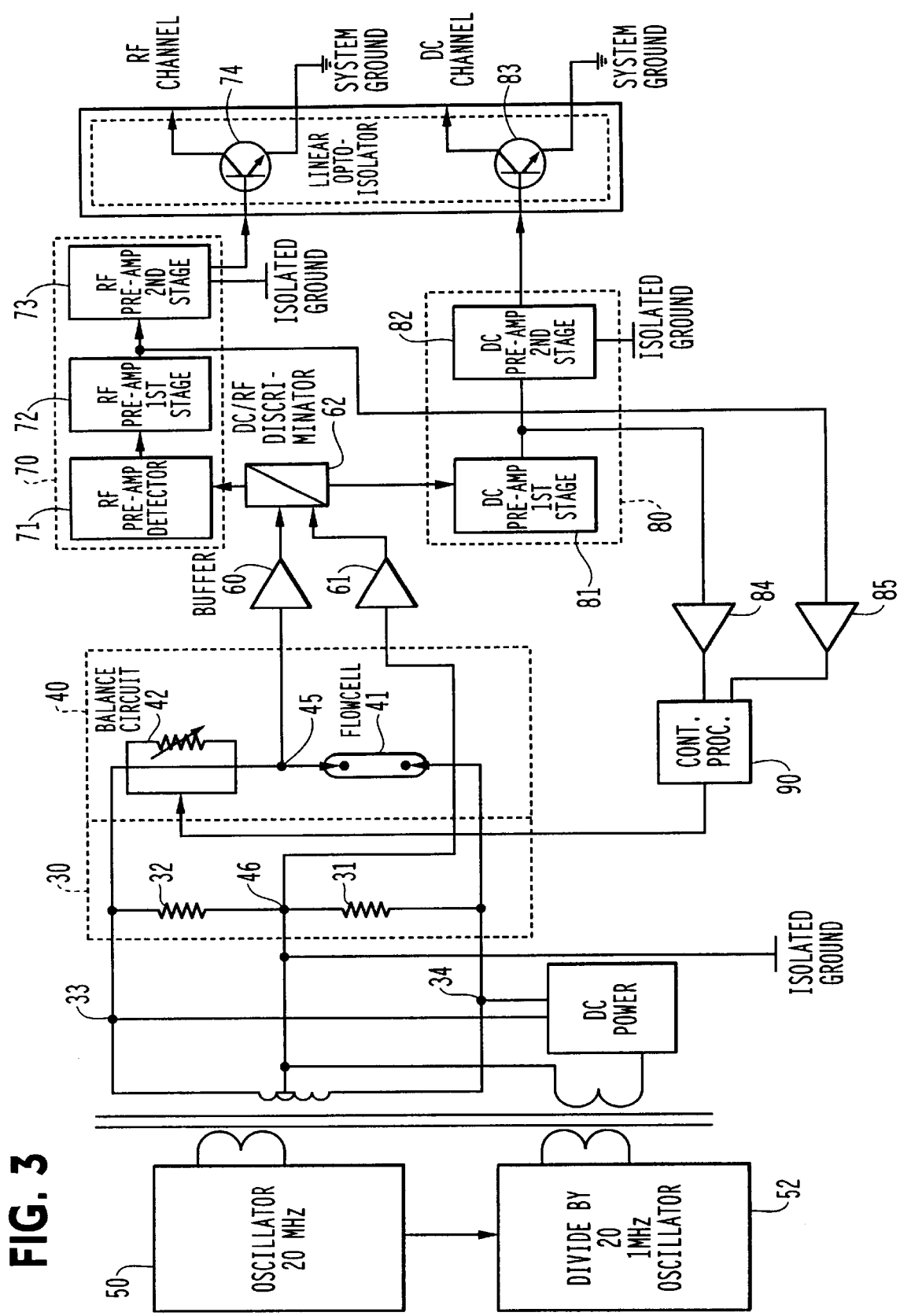
FIG. 3 diagrammatically illustrates a DC/RF excited bridge architecture, based upon the Wheatstone bridge circuit of FIG. 2 and having opto-isolator coupling for galvanic isolation, for detecting particles/cells in a flowcell measurement aperture of a particle flow analyzer.

FIG. 3 diagrammatically illustrates a potential bridge architecture based upon the standard Wheatstone bridge circuit of FIG. 2, described above, but which is stimulated by means of an RF oscillator, as an approach to provide for the detection of particles/cells that may be present in a flowcell measurement aperture of a particle flow analysis system of the type shown in FIG. 1, described above. Like the Wheatstone bridge of FIG. 2, the DC/RF-driven bridge of FIG. 3 includes a first voltage dividing circuit branch 30 containing a pair of linear impedance circuit elements 31 and 32, such as resistors of equal value, that are connected in series between bridge stimulation terminals 33 and 34.

The bridge stimulation terminals 33 and 34 are coupled to an RF oscillator 50, such as a 20 MHz sinusoidal oscillator producing an output voltage at 40 Vpp. The output of RF oscillator 50 may also be inductively (transformer-) coupled to a rectification and scaling circuit 52, which is operative to appropriately scale down the RF voltage to provide isolated DC power to the bridge proper, and to downstream signal processing circuits.

The DC/RF bridge further includes a second voltage divider branch 40 connected between the bridge stimulation terminals 33 and 34. One of the impedance elements of the second branch 40 is a flowcell 41, whose characteristic value (impedance) is expected to vary due to the presence of a particle, in particular, a blood particle in the flowcell s measurement aperture. The other impedance element 42 is comprised of a resistor-capacitor circuit network that is configured to model or very closely approximate the behavior of the flowcell 41, tracking (non-linear) variations in impedance the flowcell in response to changes in the environment, such as temperature and the conductivity of a fluid through its measurement aperture, and keep the bridge in balance in a self-adjusting manner.

For this purpose, a DC component as well as a phase component in the RF/DC output signal obtained from output nodes 45 and 46 of the bridge are used to maintain closed loop balancing. As will be described, these DC and RF components are fed back to respective threshold comparators 84 and 85, the outputs of which are monitored by the flowcell's control processor 90 to detect and correct for bridge imbalances. In particular, the DC/RF output pulses from the output node 45 between the circuits 41 and 42 of the flowcell-containing branch, and the output node 46 between reference branch resistors 31 and 32 are coupled through respective high speed buffer amplifiers 60 and 61 and passed therefrom to a DC/RF discriminator 62, which is operative to separate the DC and RF components from the composite signal produced at output nodes 45,46.

The RF component is coupled to an RF conditioning circuit path 70 comprised of an RF pre-amp detector 71 coupled in cascade with first and second RF pre-amp stages 72 and 73. The output of the second RF pre-amplifier stage 73 is coupled through a linear opto-isolator 74 to downstream RF interface circuitry (DC restoration, and Peak Detection circuits) for appropriate pulse sizing and sorting. In like manner, the DC component is coupled to a DC conditioning circuit path 80 comprised of cascaded first and second DC pre-amp stages 81 and 82. The output of the second DC pre-amp stage 82 is coupled through a linear opto-isolator 83 to downstream DC interface circuitry. The outputs of the first DC pre-amp stage 81 and the RF preamplifier stage 72 are coupled to respective threshold comparators 84 and 85, the outputs of which are monitored by the flowcell control processor 90 to detect and correct bridge imbalances, such as those that may be attributable to small impedance drifts due to the flowcell proper, ISO-TON® conductivity, etc.

Now although the potential RF/DC bridge circuit architecture of FIG. 3 ostensibly provides an alternative to a conventional change-in-reactance Hartley oscillator referenced above, our investigation of its performance and circuit properties has revealed that it is very 'noisy' and needs to be modified in order to realize a commercially practical embodiment for conducting accurate flowcell measurements.

More particularly, a first aspect that requires adjustment involves the fact that the input impedance of the output coupling buffer (typically on the order of 3 pF–5 pF) undesirably loads down the output signal due to the change in the impedance of the flowcell as a blood particle passes through it. As will be discussed in detail below, the impedance of the flowcell is both resistive and capacitive. This reactance couples with the input impedance of the buffer and acts as a second order filter that substantially suppresses the desired signal.

Secondly, the large resistor values in the bridge network, which are typically used in a Wheatstone bridge network to optimize signal detection, together with the parasitic reactances of their leads act as lumped low pass filters. It is common knowledge that a Wheatstone bridge network typically produces erroneous output measurements due to parasitic resistances inherent in the network. These parasitics can also vary due to temperature, conductivity or other conditions present in the environment of the object parameter being measured. In most standard applications, measurements are conducted at DC or at very low frequencies close to DC (e.g., 60 Hz). The measurement error in the bridge under these conditions is negligible.

However, at very high frequencies (e.g. on the order of 20 MHz or above, commonly used in medical instrumentation), large resistor values (e.g., on the order of several tens of kilohms) coupled with parasitic capacitance inherent in the bridge network (typically on the order of 1–3 pF) further degrade the performance of the bridge and make measurements unpredictable and inaccurate. As a non-limiting example, a resistance 38.5 K$\Omega$ and a parasitic capacitance on the order of 1 pF yields a roll-off frequency of $\frac{1}{2}\pi*38.5$ K$\Omega*1$ pF=4.1 MHz, which significantly reduces the energy in a 20 MHz excitation source used to drive the bridge of FIG. 3, and makes RF measurements effectively impossible.

In order to gain an appreciation of the performance of a DC/RF driven bridge that led to a modification to realize a working embodiment of the invention, the present inventors conducted an analysis of a typical flowcell and its impedance characteristics. Using a spectrum analyzer test set-up as diagrammatically illustrated in FIG. 4, the impedance of a flowcell 100 of the type used in a system of the type diagrammatically illustrated in FIG. 1 was measured as a function of frequency. The output of the sweep oscillator 101 of the test circuit set-up of FIG. 4 was swept over a prescribed range (e.g., 0–40 MHz), using the tracking generator of the spectrum analyzer 103. A voltage divider resistor 105 coupled in series with the flowcell 100 has negligible loading effects, due to the flowcell and parasitic reactances of the test set-up.

Figure 4:
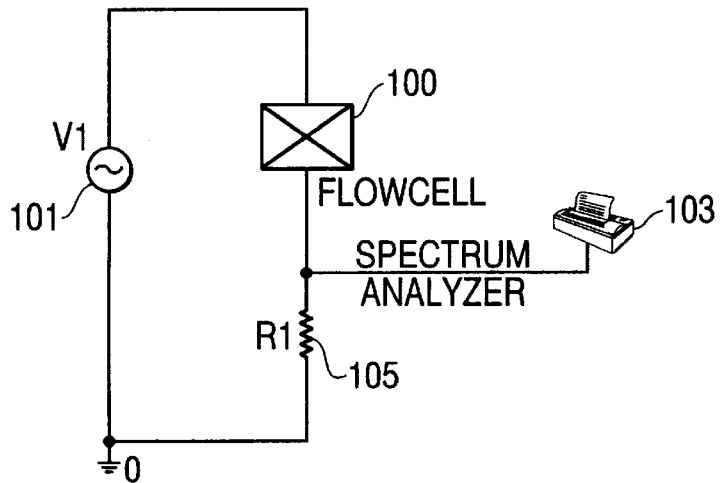
FIG. 4 diagrammatically illustrates a spectrum analyzer test set-up for measuring variation in impedance of a flowcell with frequency.
Figure 5:
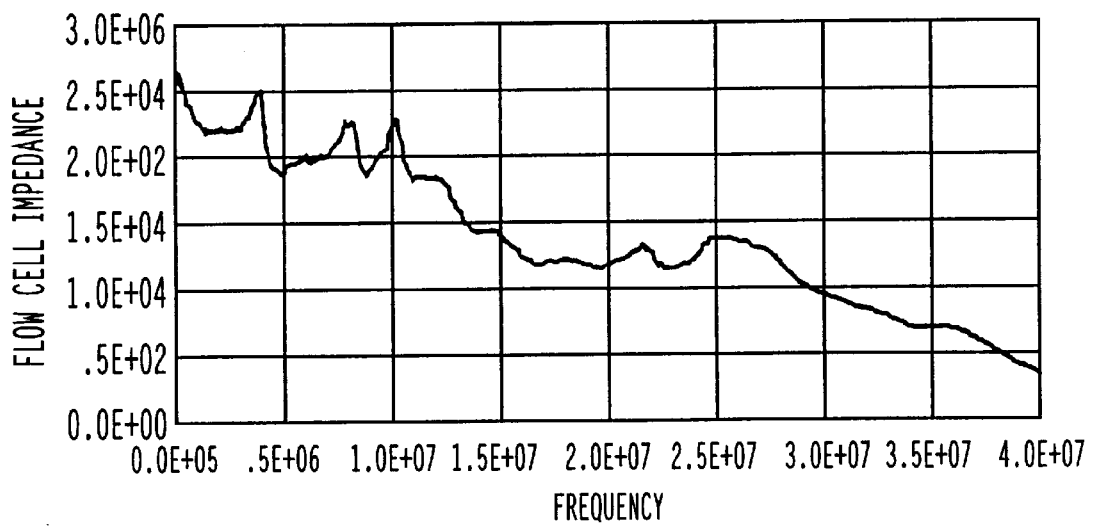
FIG. 5 is an impedance plot obtained from the flowcell measurement test set up of FIG. 4.
Figure 6:
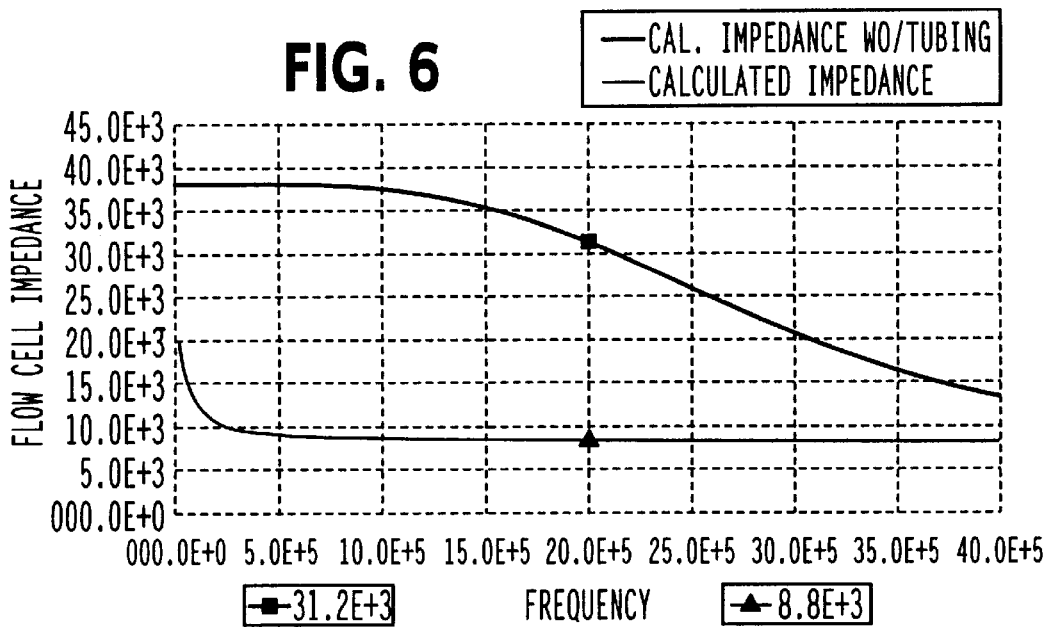
FIG. 6 is an impedance plot of a mathematical (electrical) flowcell model.

FIG. 5 is an impedance plot obtained from the flowcell measurement test set up of FIG. 4, while FIG. 6 is an impedance plot of a mathematical (electrical) flowcell model.

Using field theory, the flowcell was further analyzed to determine its approximate capacitance and reactance. In this analysis, the following conditions were assumed: 1—ISOTON is a conductor; 2—the wavelength of the test frequency (20 MHz) is considerably greater than length (Lap) and width or diameter (Dap) dimensions of the flowcell aperture, which are of an order approximating the size of the particle passing through it; and 3—a lumped parasitic capacitance of the flowcell.

Figure 7:
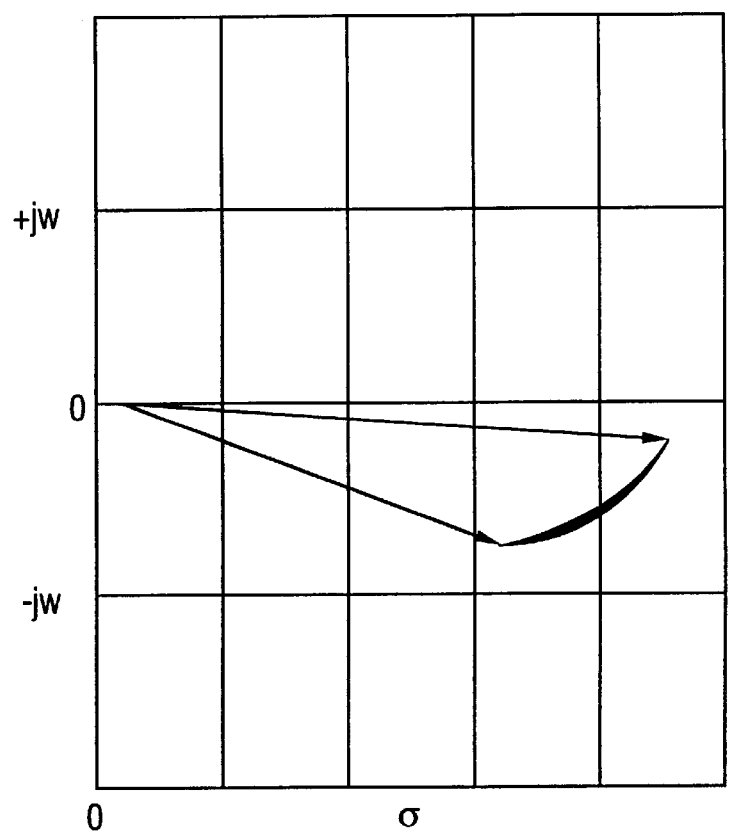
FIG. 7 shows the variation in the complex plane operating point of an empty flowcell as its capacitance is varied.

FIG. 7 is a plot of the variation in the operating point of an empty flowcell (i.e., a flowcell with no particle) in the complex plane, as its capacitance is varied between 0.05 pF and 0.3 pF (values obtained from field theory). The flowcell impedance values approximate both actually measured and modeled values. Using these measured and calculated values, the approximate 'change' in impedance of the flowcell due to the presence of a particle in the measurement aperture was determined, and plotted in FIG. 8.

Figure 8:
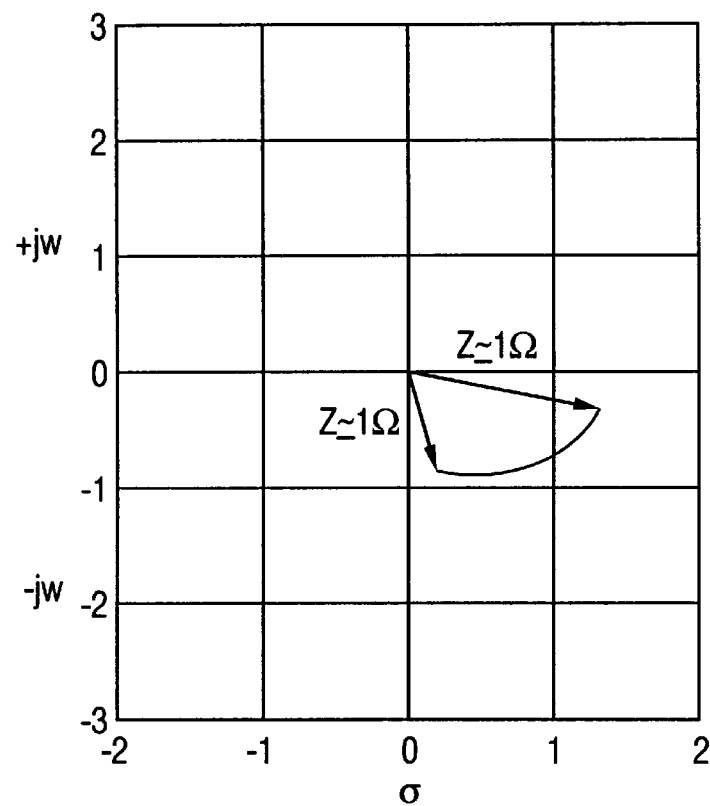
FIG. 8 is an impedance variation diagram showing the change in impedance of a flowcell due to the presence of a particle.

As can be seen from the impedance variation diagram of FIG. 8, the change in the impedance of the flowcell due to the presence of a particle (such as a blood cell) is extremely small (on the order of only about 10 in 10,000). It is readily apparent, therefore, that a conventional Wheatstone bridge circuit design, such as that of FIG. 3, will not successfully detect very minute complex electrical changes in its network and, more specifically, in a very high frequency environment, such as a flowcell employing a high frequency RF signal to measure cell density.

Figure 9:
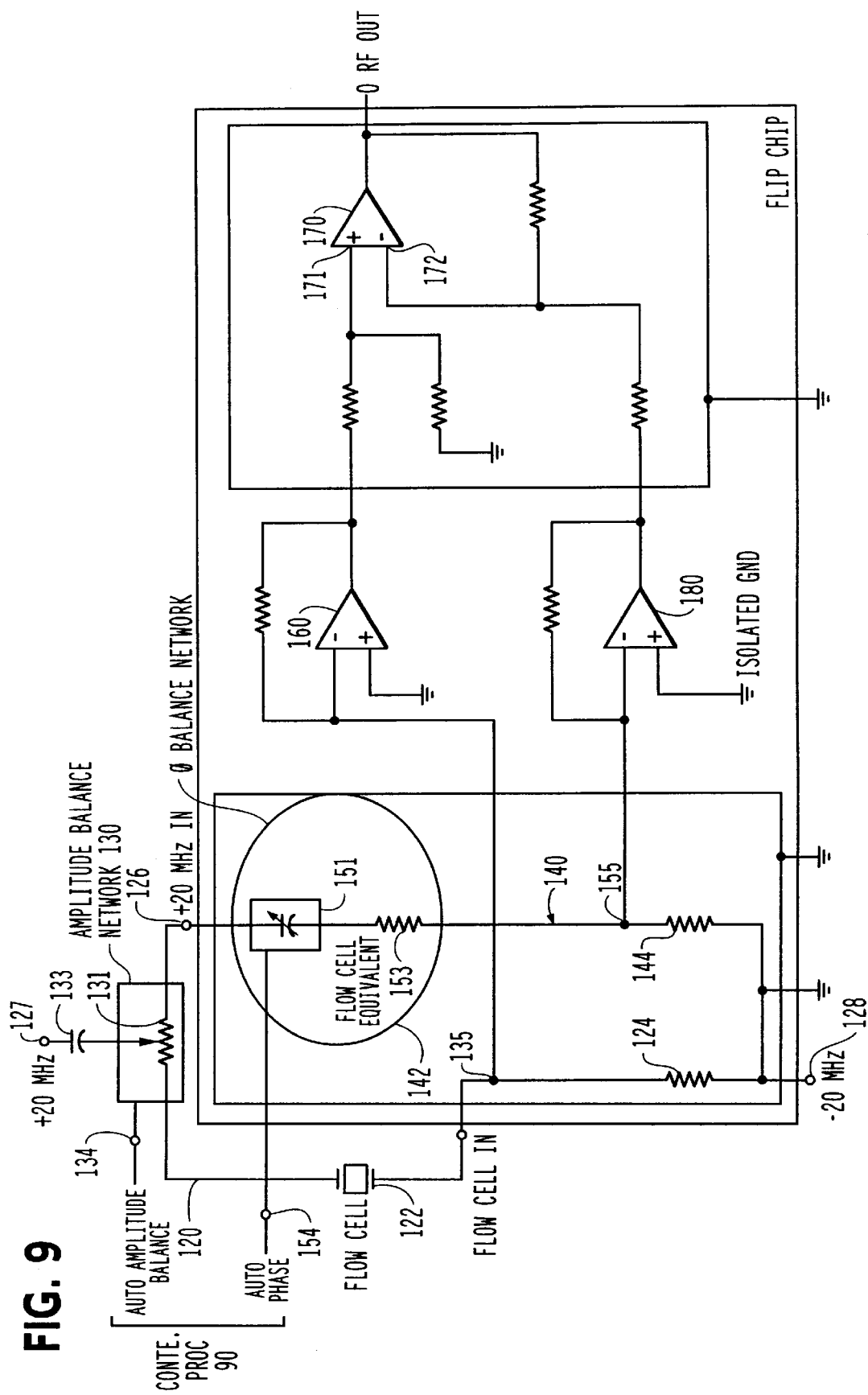
FIG. 9 shows an DC/RF-excited bridge-configured detector having automatic flowcell-model amplitude and phase balance circuits in accordance with the present invention.

This shortcoming of a conventional Wheatstone bridge approach is remedied by the modified bridge architecture of FIG. 9, which shows a differential amplifier-coupled, DC/RF-stimulated, bridge-configured detector having automatic amplitude and phase balance circuits in accordance with the present invention, the output of which is coupled to the downstream amplifier and opto-isolator components of FIG. 3, detailed above.

As will be described, the automatically balanced bridge detector architecture of the invention is preferably implemented using flip-chip technology, using a bare IC die that virtually eliminates capacitive reactance with bridge components, thereby making the bridge virtually immune to signal loading by parasitic capacitance of the coupling circuits. The DC/RF-driven bridge detector architecture of the invention is operative to measure, in the presence of very large common mode noise commonly encountered in a bridge environment, and especially in a very high frequency environment, extremely small and complex electrical signals, reliably and virtually unaffected by parasitic resistances that commonly exist in the network.

As noted above with reference to the flowcell impedance change plot of FIG. 8, the change in impedance of the flowcell due to the presence of a particle in the cell's measurement aperture is extremely small—on the order of only $10 \mu\Omega$. Since it is well established that the characteristic impedance of the flowcell is determined by its aperture length $L_{ap}$ and diameter $D_{ap}$, the diameter being the most dominant factor, it is clear that variations in the dimensions of the flowcell (which are attributable to tolerances in the flowcell manufacturing process) will significantly change the operating point (impedance) of the flowcell. Therefore, in order to maintain adequate performance of the RF pre-amplifier in the RF conditioning circuit path, it would appear that the dimensions of the flowcell should be tightly controlled. Unfortunately, this tolerance requirement places a significant strain on the manufacturing process, and makes manufacturing of flowcells difficult and expensive.

On the other hand, the automatic amplitude and phase balanced bridge circuit architecture of FIG. 9 makes RF detection and measurement virtually insensitive to such flowcell dimensional variations as commonly occur in manufacturing processes. More particularly, the DC/RF bridge design of FIG. 9 comprises a first voltage dividing circuit branch 120 containing a flowcell 122 and a first linear impedance element (resistor) 124 connected in a series circuit path between first and second bridge stimulation terminals 126 and 128, across which +/−20 MHz voltages are applied. The peak-to-peak excitation voltage applied across terminals 126 and 128 should be sufficiently large to optimize the signal-to-noise ratio between output nodes 135 and 155.

Also coupled in circuit with the flowcell 122 and the +20 MHz terminal 126 is an automatic amplitude balance circuit 130 comprising a variable resistor 131, having its variable tap coupled through a capacitor 133 to a +20 MHz terminal 127. The value of variable resistor 131 is controlled by an amplitude control signal coupled to terminal 134. The first bridge output node 135 is coupled to the common connection between flowcell 122 and the first linear impedance element 124.

The DC/RF bridge design of FIG. 9 further comprises a second voltage dividing circuit branch 140 containing a flowcell circuit model 142 and a second linear impedance element (resistor) 144 connected in a series circuit path between the first and second bridge stimulation terminals 126 and 128. The flowcell circuit model 142, which functions as an automatic phase balance circuit, comprises a variable capacitor 151 and a linear resistor 153, coupled in circuit between the +20 MHz terminal 126 and the second bridge output node 155. The value of variable capacitor 151 is controlled by a phase control signal coupled to terminal 154.

Installing linear elements 124 and 144 in the bottom legs of the bridge architecture of FIG. 9 virtually eliminates second order Laplacian effects associated with coupling circuits. The input capacitance of each coupling circuit together with the linear resistor (124/144) forms a first order filter having a cut off frequency determined by the value of the resistor and the input capacitance of an associated coupling amplifier.

The first bridge output node 135 is coupled to a first front-end signal gain, current amplifier 160, the output of which is coupled to a first input 171 of a difference amplifier 170. A second input 172 of difference amplifier 170 is coupled to the output of a second front-end amplifier 180, the input of which is coupled to the second bridge output node 155. The difference amplifier 170 is operative to subtract common-mode noise inherent in the network, as well as residual noise caused by the imbalance in the two branches 120 and 140 of the bridge. The output of the difference amplifier 170 is coupled to a DC/RF discriminator and associated downstream processing circuitry corresponding to that employed to process the output of the bridge design of FIG. 3, described above.

By virtue of its differential coupling configuration and the linear opto-isolation described above, the modified bridge implementation of FIG. 9 provides what is effectively a "floating" bridge and associated pulse detection circuits. Rather than being referenced to common 'metallic' ground, as are conventional bridge networks, the bridge circuit of FIG. 9 galvanically isolates the front-end signal detection circuits from downstream signal processing and filtering circuits (so that there is no metallic connection path therebetween).

A fundamental drawback to using a common ground reference is the need to employ extensive filtering in the signal detection and processing circuits, in order to remove unwanted high frequency noise components that are buried in the signal. The bandwidths of these filters have to be made narrow enough to minimize the effects of noise and to optimize the signal-to-noise ratio. However, the narrow bandwidth of the filter, in addition to filtering noise, also causes signal attenuation. As a result, compensation for the loss of signal amplitude due to attenuation requires a gain adjustment circuit; this, in turn, undesirably amplifies the inherent noise of the processing circuits.

The "floating" scheme of FIG. 9, on the other hand, prevents high frequency components, inherent in the oscillator, from interfering with the actually detected pulse. This means that the filter bandwidths in the downstream signal processing circuits can be made much wider to accommodate all of the signal energy density, with virtually no interference from noise in the signal path.

As noted earlier, one of the fundamental drawbacks of a standard Wheatstone bridge network is the degradation of signal quality and, in cases involving very high frequency detection schemes, such as RF pulse detection, a complete loss of signal. This signal degradation is mainly due to resistances and reactances parasitic in its connecting components. For a properly functioning RF pre-amp, the parasitics inherent in the bridge must be virtually eliminated, i.e. the coupling amplifiers 160, 170 and 180 must have very low input capacitance, which real life components do not typically exhibit.

In accordance with a preferred implementation, the front end coupling amplifiers employed in the bridge architecture of FIG. 9 may be commercially available components, such as AD9631 model components manufactured by Analog Devices. These devices have been found to exhibit an excellent gain-bandwidth product, slew rate and offset specifications required for flowcell particle measurements. However, because the input capacitance C of this coupling amplifier is not insignificant (on the order of $3\ pF \leq C \leq 7\ pF$, which is typical of high performance amplifiers), it introduces substantial loading at high frequencies, and must be compensated.

Pursuant to a further aspect of the invention, this is accomplished by mounting the output signal coupling amplifier circuits using flip-chip technology, and thereby make the bridge virtually immune to signal loading by the coupling circuits. In particular, virtually all signal loading due to the input impedance of the coupling amplifiers is eliminated by flip-chip mounting the bare die of the amplifier integrated circuit. It has been found that when the Analog Devices part No. AD9631, referenced above, is flip-chip mounted to the printed circuit board containing the other components of the bridge, the input capacitance of the coupling amplifier is effectively reduced to less than 0.3 pF, and thereby significantly reduces loading at the high operational frequency of interest (e.g., 20 MHz). Such mounting also affords high circuit integration at lower manufacturing costs and improved circuit performance.

In addition to 'floating' the network and using flip-chip mounting, as described above, the modified bridge implementation of FIG. 9 incorporates automatic amplitude and phase balancing circuits 130 and 142, respectively. As pointed out earlier with reference to FIGS. 1 and 2, a typical Wheatstone bridge network contains three linear elements. When measuring a change in the characteristic of an environment, it is common practice to physically place in the environment a fourth element, whose value varies as a function of the environment being measured. It is also a common practice to maintain a "good" balance between the two voltage divider branches of the bridge, so as to minimize the effects on common mode noise.

In the modified Wheatstone bridge architecture of the present invention, the fourth element is a flowcell 122. Unlike typical bridge elements, the flowcell has non-linear (both resistive and capacitive) characteristics, as described above with reference to FIGS. 4–8B, and is prone to continuous impedance changes due to temperature, and conductivity of a fluid (such as ISOTON®) through its measurement aperture. To compensate for this non-linear behavior, the bridge circuit of FIG. 9 also employs the balancing circuits 130 and 142, whose characteristics closely resemble those of the flowcell proper.

The values of the variable components of automatic amplitude and phase balancing circuits are controllably adjusted by the flowcell control processor 90 during a calibrate mode of operation to correct bridge imbalances, such as those that may be attributable to small impedance drifts due to the flowcell proper, ISOTON conductivity, etc. Bridge calibration may be performed prior to a blood sample analysis, by flowing a blood sample-free saline solution through the flowcell, and monitoring the bridge's DC voltage output as extracted by the DC/RF discriminator 62 of FIG. 3, referenced above. If there has been a drift or offset in the flowcell impedance, for example due to temperature, the bridge's control processor will adjust the parameters of the flowcell balancing circuitry so as to drive the bridge's differential voltage output to zero.

Namely, during bridge calibration, the control processor is operative to 'tune' the resistive and capacitive elements of the balance circuit so as to mirror the characteristics of the flowcell, and thereby automatically balancing the amplitude and phase in the bridge, minimizing common mode noise generated by the network, and optimizing the signal-to-noise ratio. This automatic adjustment makes the network virtually immune to flowcell load tolerances and varying impedances due to the environment.

As will be appreciated from the foregoing description, shortcomings of conventional flowcell detectors, such as change-in-reactance based, RF Hartley oscillator-configured circuits for measuring both cell volume and internal cellular conductivity are effectively obviated by the differential DC/RF bridge-configured detector of the present invention. The respective legs of the bridge, which contain both the flowcell proper, and an adjustable flowcell circuit model, are differentially coupled through output amplifier circuits and galvanically isolated from sources of signal degradation that would otherwise substantially impair the ability of the bridge to conduct accurate particle detection measurements. Effectively floating the bridge serves to galvanically isolate the front-end signal detection circuits. As a result, filter bandwidths in the downstream signal processing circuits can be made much wider to accommodate all of the signal energy density, with virtually no interference from noise in the signal path.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein, but intend to cover all such changes and modifications as are obvious to one of ordinary skill in the art.

What is claimed:

1. An apparatus for measuring a parameter of an object comprising:

a bridge circuit having a first voltage divider branch adapted to coupled in circuit with said object, and a second voltage divider branch containing an electrical balancing network that is configured to electrically model said object, and controllably balance variations in amplitude and phase in electrical behavior of said object for changes in environmental conditions of said object, said electrical balancing network including a controllably adjustable amplitude balancing circuit and a controllably adjustable phase balancing circuit coupled therewith;

a source of electrical energy, including radio frequency (RF) energy, coupled to said bridge circuit and being operative to cause said object to exhibit a change in an electrical characteristic thereof in accordance with a variation of said parameter; and a detector circuit coupled to said bridge circuit and being operative to measure said parameter of said object in accordance with said change in said electrical characteristic of said object, and including a DC/RF signal discriminator circuit that is operative to extract respective amplitude and phase components of a signal representative of said change in said electrical characteristic of said object, and to controllably adjust said amplitude balancing circuit in accordance with said amplitude component, and to controllably adjust said phase balancing circuit in accordance with said phase component, so as to automatically compensate for amplitude and phase variations in said electrical behavior of said object.

2. An apparatus according to claim 1, wherein said parameter comprises a particle in a measurement aperture of a flowcell, and wherein said detector circuit is operative to detect an attribute of said particle in accordance with a change in electrical impedance of said flowcell.

3. An apparatus according to claim 2, wherein said bridge circuit is configured so that said detector circuit is effectively insensitive to variations in electrical loading thereof due to variations in characteristics of said flowcell exclusive of the presence of a particle.

4. An apparatus according to claim 1, wherein said detector circuit includes output coupling amplifier circuitry configured as a flip-chip mounted integrated circuit.

5. An apparatus according to claim 1, wherein said bridge circuit is configured to electrically float and thereby galvanically isolate said bridge circuit from said source of RF energy.

6. An apparatus according to claim 1, wherein said bridge circuit is configured so that said detector circuit is effectively insensitive to variations in electrical loading thereof by said object.

7. An apparatus according to claim 1, wherein said detector circuit is opto-isolator coupled to downstream signal processing circuitry.

8. For use with a system in which a carrier fluid containing particles is supplied to a flowcell having a measurement aperture, a circuit for detecting an attribute of a particle present in said measurement aperture of said flowcell comprising:

a bridge circuit having circuit branches thereof coupled to a source of electrical energy including radio frequency (RF) energy, said bridge circuit having said flowcell coupled therein, and including an electrical balancing circuit that is configured to electrically model said flowcell, and controllably balance variations in amplitude and phase in electrical behavior of said flowcell for changes therein, said electrical balancing network including a controllably adjustable amplitude balancing circuit and a controllably adjustable phase balancing circuit coupled therewith; and a detector circuit coupled to said bridge circuit and being operative to generate an output signal representative of said attribute of a particle present in said flowcell in accordance with a change in impedance of said flowcell associated with the presence of said particle in said measurement aperture, and including a signal discriminator circuit that is operative to extract respective amplitude and phase components of a signal representative of said change in impedance of said flowcell, and to controllably adjust said amplitude balancing circuit in accordance with said amplitude component, and to controllably adjust said phase balancing circuit in accordance with said phase component, so as to automatically compensate for amplitude and phase variations in said electrical behavior of said flowcell.

9. A circuit according to claim 8, wherein said bridge circuit is configured so that said detector circuit is effectively insensitive to variations in electrical loading thereof due to variations in characteristics of said flowcell exclusive of the presence of a particle in said measurement aperture.

10. A circuit according to claim 8, wherein said detector includes output coupling amplifier circuitry configured as a flip-chip mounted integrated circuit.

11. A circuit according to claim 8, wherein said bridge circuit is configured to electrically float and thereby galvanically isolate said bridge circuit from said source of said RF energy.

12. A circuit apparatus according to claim 8, wherein said bridge circuit is galvanically isolated from a source of signal degradation, and is configured so that said detector circuit is effectively insensitive to variations in electrical loading thereof by said flowcell.

13. A circuit according to claim 8, wherein said detector circuit is opto-isolator coupled to downstream signal processing circuitry.

14. For use with a system in which a carrier fluid containing particles is supplied to a flowcell having a measurement aperture, a method for detecting an attribute of a particle present in said measurement aperture of said flowcell comprising the steps of:

(a) providing a bridge circuit having branches thereof coupled to a source of electrical energy including radio frequency (RF) energy;

(b) installing said flowcell in a branch of said bridge circuit;

(c) installing in a branch of said bridge circuit an electrical balancing circuit, that is configured to electrically model behavior of said flowcell for changes in environmental conditions of said flowcell, and controllably balance variations in amplitude and phase in electrical behavior of said flowcell for changes therein, said electrical balancing network including a controllably adjustable amplitude balancing circuit and a controllably adjustable phase balancing circuit coupled therewith;

(d) monitoring electrical variations in said bridge circuit and generating an output signal representative of said attribute of a particle present in said flowcell in accordance with a change in impedance of said flowcell associated with the presence of said particle in said measurement aperture; and (e) extracting respective amplitude and phase components of said output signal representative of said change in impedance of said flowcell, and controllably adjusting said amplitude balancing circuit in accordance with said amplitude component, and controllably adjusting said phase balancing circuit in accordance with said phase component, so as to automatically compensate for amplitude and phase variations in said electrical behavior of said flowcell.

15. A method according to claim 14, wherein step (d) comprises monitoring said variations in said bridge circuit through differentially coupled flip-chip mounted amplifier circuitry.

16. A method according to claim 14, wherein said bridge circuit is configured to electrically float and thereby galvanically isolate said bridge circuit from said source of RF energy.

* * * * *